(12) United States Patent
Gray et al.

(10) Patent No.: US 6,455,312 B1
(45) Date of Patent: Sep. 24, 2002

(54) REGENERATION SYSTEM FOR GRAPE AND USES THEREOF

(75) Inventors: Dennis J. Gray, Howey-in-the-Hills; Jayasankar Subramanian, Tavares; Richard E. Litz, Homestead, all of FL (US)

(73) Assignee: University of Florida, Gainesville, FL (US)

( * ) Notice: Subject to any disclaimer, the term of this patent is extended or adjusted under 35 U.S.C. 154(b) by 0 days.

(21) Appl. No.: 09/311,823

(22) Filed: May 13, 1999

Related U.S. Application Data

(63) Continuation-in-part of application No. 09/087,285, filed on May 29, 1998.
(60) Provisional application No. 60/085,711, filed on May 15, 1998.

(51) Int. Cl.[7] .............................. C12N 5/00; C12N 5/02; A01H 5/00
(52) U.S. Cl. .................... 435/430.1; 435/431; 435/430; 435/420; 435/410; 800/298
(58) Field of Search ................................ 800/278, 298; 435/430, 430.1, 431, 420, 410

(56) References Cited

U.S. PATENT DOCUMENTS

| | | | | |
|---|---|---|---|---|
| 4,532,733 A | * | 8/1985 | Krul | 47/58 |
| 5,084,082 A | | 1/1992 | Sebastian | 71/90 |
| 5,238,835 A | | 8/1993 | McKersie et al. | 435/240.45 |
| 5,648,594 A | | 7/1997 | Davis et al. | 800/200 |
| 5,914,270 A | | 6/1999 | Coutos-Thevenot et al. | 435/430 |

FOREIGN PATENT DOCUMENTS

| | | | | |
|---|---|---|---|---|
| FR | 2 710 234 | 9/1993 | ............ | A01H/4/00 |
| WO | Wo 93/11660 | 6/1993 | ............ | A01H/7/00 |
| WO | WO 93/23529 | 11/1993 | ............ | C12N/5/04 |
| WO | WO 94/13787 | 6/1994 | ............ | C12N/5/04 |
| WO | WO 95/19102 | 7/1995 | ............ | A01H/4/00 |

OTHER PUBLICATIONS

Mauro et al., Plant Science 112, 97–106, 1995.*
Kikkert et al., Plant Cell Reports, 15:311–316, 1996.*
Regner et al., Mitteilungen Klostereuburg 46:105–113, 1996.*
Coutos–Thevenot et al., Plant Cell, Tissue and Organ Culture 29: 125–133, 1992.*
Stamp et al., Scientia Horticulturae, 35: 235–250, 1988.*
Compton et al., Effects of sucrose and methylglyoxal bis–(guanyldrazone) on controlling grape somatic embryogenesis, *Vitis* 35:1–6 (1996).
Coutos–Thevenot et al., "Somatic embryrogenesis from grapevine cells. I–Improvement of embryo development by changes in culture conditions," *Plant Cell, Tissue and Organ Culture* 33:91–103 (1993).

Goebel–Tourand et al., "Arrest of somatic embryo development in grapevine: histological characterization and the effect of ABA, BAP and zeatin in stimulating plantlet development," *Plant Cell, Tissue and Organ Culture* 33:91–103 (1993).
Goussard et al., "The elimination of fanleaf virus form grapevines using in vitro somatic embryogenesis combined with heat therapy," *S. Afr. J. Enol. Vitic.* 13:81–83 (1992).
Goussard et al., "The effectiveness of in vitro somatic embryogenesis in eliminating fanleaf virus and leafroll associated viruses from grapevines," *S. Afr. J. Enol. Vitic.* 12:77–81 (1991).
Gray et al., "In vitro micropropagation and plant establishment of muscadine grape cultivars (Vitis rotundifolia)," *Plant Cell, Tissue and Organ Culture* 27:7–14 (1991).
Gray et al., "Inititation and maintenance of long term somatic embryogenesis from anthers and ovaries of Vitis longii 'Microsprema," *Plant Cell, Tissue and Organ Culture* 9:73–80 (1987).
Gray et al., "Biotechnology of perennial fruit crops," *Grape* 229–262 (1992).
Gray, D.J., "Somatic embryogensis and plant regeneration from immature zygotic embryos of muscadine grape (Vitis rotundifolia) cultivars," *American Journal of Botany* 79:542–546 (1992).
Hébert et al., "Optimization of biolistic transformation of embryogenic grape cell suspensions," *Plant Cell Reports* 12:585–589 (1993).
Hébert–Soulé et al., Phosphinothricin stimulates somatic embryogenesis in grape (Vitis sp. L.), *Plant Cell Reports* 14:380–384 (1995).
Kikkert et al., "Transgenic plantlets of 'Chancellor' grapevine (Vitis sp.) from biolistic transformation of embryogenic cell suspensions," *Plant Cell Reports* 15:311–316 (1996).
Kranstanova et al., "Transformation of grapevine rootstocks with the coat protein gene of grapevine fanleaf nepovirus," *Plant Cell Reports* 14:550–554 (1995).
Krul et al., "Formation of adventitious embryos in callus cultures of 'Seyval', a French hybrid grape[1]," *J. Amer. Soc. Hort. Sci.* 102:360–363 (1977).
Martinelli et al., "Somatic embryogenesis from leaf–and petiole–derived callus of *Vitis rupestris*," *Plant Cell Reports* 12:207–210 (1993).
Matsuta, N., "Effect on auxin somatic embryogenesis from leaf callus in grape (Vitis spp.)," *Jap. J. Bread* 42:879–883 (1992).

(List continued on next page.)

Primary Examiner—Bruce R. Campell
Assistant Examiner—Anne Marie Grunberg
(74) Attorney, Agent, or Firm—Clark & Elbing LLP

(57) ABSTRACT

The invention features methods of producing a plant or a mature somatic embryo from an embryogenic cell or embryogenic culture. The method includes the steps of: (a) providing a liquid culture that includes an embryogenic cell; (b) recovering embryogenic cell from the culture; (c) transferring the embryogenic cell to a second culture; and (d) growing a mature somatic grape embryo from the embryogenic cell.

3 Claims, 2 Drawing Sheets

OTHER PUBLICATIONS

Matsuta et al., Embryogenic cell lines form somatic embryos of grape (*Vitis vinifera L.*), *Plant Cell Reports* 7:684–687 (1989).

Mauro et al., "Stimulation of somatic embryogenesis and plant regeneration from another culture of *Vitis vinifera* cv. Cabernet–Sauvignon," *Plant Cell Reports* 5:377–380 (1986).

Mullins et al., "Plantlets from cultured anthers of Vitis species and hybrids," In Proc. of $3_{rd}$ Int'l Symp. on Grape Breeding, *University of California* (Davis) pp. 111–119 (1980).

Mullins et al., "Somatic embryos and plantlets from an ancient clone of the grapevine (cv. Cabernet–Sauvignon) by apomixis in vitro," *J. of Exp. Bot.* 27:1022–1030 (1976).

Newton et al., "The ontogeny of somatic embryos from in vitro cultured grapevine anthers," *S. Afr. J. Enol. Vitic.* 11:70–75 (1990).

Pearce et al., "Effects of chilling and ABA on [$^3$H] gibberellin $A^4$ metabolism in somatic embryos of grape (*Vitis vinifera L.* x. *rupstris* Scheele)" *Plant Physiol.* 80:381–385 (1987).

Perl et al., "Establishment of an agrobacterium–mediated transformation system for grape (*Vitis vinifera L.*): the role of antioxidants during grape–Agrobacterium interactions," *Nature Biotechnol.* 14:624–628 (1996).

Perl et al., Regeneration and transformation of grape (*Vitis vinifera L.*), *Plant Tissue Culture and Biotechnology* 2:187–193 (1996).

Rajasekaran et al., "Embryos and plantlets from cultured anthers of hybrid grapevines," *J. of Exp. Bot.* 116: 399–407 (1979).

Rajasekaran et al., "Influence of genotype and sex–expression on formation of plantlets by cultured anthers of grapevine," *Agronomie* 3:233–238 (1983).

Rajasekaran et al., "Dormancy in somatic embryos and seeds of Vitis: changes in endogenous abscisic acid during embryogeny and germination," *Planta* 154:139–144 (1982).

Reustle et al., "Plant regeneration of grapevine (Vitis sp.) protoplasts isolated from embryogenic tissue," *Plant Cell Reports* 15:238–241 (1995).

Robacker, C., "Somatic embryogensis and plant regeneration from muscadine grape leaf explants," *Dept. of Hort-Science* 28:53–55 (1988).

Scorza et al., "Producing transgeneic Thompson seedless grape (*Vitis vinifera L.*) plants," *J. Amer. Soc. Hort. Sci.* 121:616–619 (1996).

Srinivasan et al., "High–frequency somatic embryo production from unfertilized ovules of grapes," *Scientia Horticulturae* 13:245–252 (1980).

Stamp et al., "Somatic embryogenesis from leaves and anthers of grapevine," *Scientia Horticulturae* 35:235–250 (1980).

Stamp et al., "Proliferative somatic embryogenesis from zygotic embryos of grapevine," *J. Amer. Soc. Hort. Sci.* 113:941–945 (1988).

Takeno et al., "Endogenous gibberellin–like substances in somatic embryos of grape (*Vitis vinifera x Vitis rupestris*) in relation to embryogenesis and the chilling requirement for subsequent development of mature embryos," *Plant Physiol.* 73:803–808 (1983).

* cited by examiner

REGENERATION SYSTEM FOR GRAPE AND USES THEREOF

CROSS-REFERENCE TO RELATED APPLICATIONS

This application is a continuation-in-part of U.S. utility application Ser. No. 09/087,285, filed May 29, 1998, and claims benefit from U.S. provisional application 60/085,711, filed May 15, 1998.

BACKGROUND OF THE INVENTION

This invention relates to methods for regenerating grape plants, and grape germplasm produced using such methods.

Grapevines are a deciduous temperate fruit crop of ancient origin. Grape production ($65 \times 10^6$ metric tons) exceeds that of any other temperate fruit crop, and ranks third after Citrus and banana production. In addition, due to its uses for fresh fruit, juice, jelly, raisins, and wine, grapes surpass all other fruit crops in value. Therefore, successful efforts to improve grapevines are likely to have a major impact on commercial viticulture.

Current methods for improving grapevines are time-consuming and labor intensive. For example, genetic improvement in grapes through conventional breeding is severely limited by a number of factors such as long pre-bearing age and varying ploidy levels. Cultivated grapes are also highly heterozygous and do not generally breed true from seeds. Moreover, grape breeding programs are expensive, long-term projects. Although plant biotechnology is an attractive alternative for genetic improvement in grapes (Kuksova et al., Plant Cell Tiss. Org. Cult. 49:17–27, 1997), in vitro genetic manipulation can be addressed only if there is an effective regeneration system. Accordingly, methods that reduce any of these problems would represent a significant advancement in the art.

SUMMARY OF THE INVENTION

We have discovered methods for growing perennial grape embryogenic cultures and for growing large quantities of somatic grape embryos from such perennial embryogenic cultures in a relatively short period using a liquid suspension culture. Several advantages are provided by the present methods. These approaches, for example, facilitate an extraordinarily high frequency of somatic embryo formation and plant regeneration. Such frequencies have not been previously reported for grapevine regeneration of any known cultivar, and render the method useful for large-scale production of clonal planting stock of grape plants. In addition, the methods produce embryos free of such common abnormalities as fusion and fasciations of somatic embryos. The methods of the invention also result in enhanced embryogenic culture initiation frequency, allowing for the production of highly embryogenic cultures that can then be successfully carried through the subsequent stages of the regeneration process to the whole plant level. Because of these advantages, the methods of the invention are especially useful in the application of biotechnology for the genetic improvement of this crop.

Accordingly, in a first aspect, the invention features a method of producing a mature somatic embryo. The method includes the steps of: (a) providing a liquid culture that includes an embryogenic cell; (b) recovering embryogenic cell from the culture; (c) transferring the embryogenic cell to a second culture; and (d) growing a mature somatic grape embryo from the embryogenic cell.

Preferably, the embryogenic cell is obtained from anthers, ovaries, ovules, floral tissue, vegetative tissue, tendrils, leaves, roots, nucellar tissue, stems, seeds, protoplasts, pericycle, apical meristem tissue, embryogenic tissue, somatic embryos, or zygotic embryos. In still other preferred embodiments, the liquid culture medium of step (a) includes a plant growth regulator (e.g., an auxin, NOA (naphthoxyacetic acid), indole-3-acetic acid (IAA), dicamba, picloram, naphthaleneacetic acid (NAA), 2,4-dichlorophenoxyacetic acid (2,4-D), a cytokinin, benzyladenine (BA), thidiazuron, zeatin, abscisic acid (ABA), or gibberellic acid (GA). In other preferred embodiments, the initiation culture medium includes at least 0.01 mg/L of a cytokinin; at least 0.1 mg/L of a carbohydrate; and at least 0.1 mg/L of a nitrogenous compound. Exemplary carbohydrates include sucrose, glucose, maltose, and glycerol. Exemplary nitrogenous compounds include potassium nitrate, calcium nitrate, anunonium nitrate, and ammonium sulfate. If desired, the embryogenic cell or the somatic embryo can be transformed with DNA (e.g., DNA encoding a gene which is capable of conferring disease resistance). The embryogenic cell can be recovered from the first culture by filtration, sedimentation, or selection. In addition, the first culture can be sieved to synchronize the formation of differentiated somatic grape embryos.

Preferably, the embryogenic cell of step (a) is obtained from a source selected from the group consisting of: an embryogenic cell produced according to steps (a) and (b) of the first aspect; a somatic grape embryo produced according to steps (a) to (d) of the first aspect; a mature somatic embryo produced according to method of the first aspect; a plantlet according to the fifth aspect; and anthers, ovaries, ovules, floral tissue, vegetative tissue, tendrils, leaves, roots, nucellar tissue, stems, seeds, protoplasts, pericycle, apical meristem tissue, embryogenic tissue, somatic embryos, or zygotic embryos from a plant produced from a mature somatic embryo produced according to the method of the first aspect.

In preferred embodiments, the method further includes transferring the somatic grape embryo to a germination medium to grow a grape plantlet.

In other preferred embodiments, the embryogenic cell, if desired, is cultured on a medium including a plant growth regulator.

The second culture can be a liquid culture or a solid culture. A preferred medium for liquid culture includes B-5 major salts and MS minor salts.

In a second aspect, the invention features a method of producing a somatic grape embryo. The method includes the general steps of: (a) providing a liquid culture comprising an embryogenic cell; (b) selecting and the embryogenic cell from the culture; (c) transferring the embryogenic cell to a second culture; and (d) growing a somatic grape embryo from the embryogenic cell.

In a third aspect, the invention features a method of producing a somatic grape embryo. The method includes the general steps of: (a) providing a liquid culture that includes an embryogenic cell and medium consisting of B-5 major salts and MS minor salts; (b) recovering the embryogenic cell from the culture; (c) transferring the embryogenic cell to a second culture; and (d) growing a somatic grape embryo from the embryogenic cell.

In a fourth aspect, the invention features a mature somatic grape embryo produced according to the method of the first aspect.

In a fifth aspect, the invention features a plantlet germinated from the mature somatic grape embryo of fourth aspect.

In a sixth aspect, the invention features a method for long-term storage of a mature somatic grape embryo. The method includes the general step of drying the embryo and storing the embryo at a temperature less than 8° C.

Preferably, the mature somatic grape embryo is produced by the method of the first aspect.

In a seventh aspect, the invention features a method for direct seeding of a somatic grape embryo. The method includes the general step of placing said somatic grape embryo in potting medium comprising sand and potting mixture.

In an eighth aspect, the invention features a method of producing a somatic grape embryo using a liquid culture medium from a perennial grape embryogenic culture. The method includes the steps of: (a) culturing a perennial grape embryogenic culture in a first liquid culture medium to grow a cellular suspension culture, the first liquid culture medium including a plant growth regulator; (b) recovering an embryogenic cell or embryogenic cell mass from the cellular suspension culture; and (c) culturing the embryogenic cell or embryogenic cell mass from the cellular suspension culture of step (b) in a second liquid culture medium to produce a somatic grape embryo.

In preferred embodiments, the method further includes transferring the somatic grape embryo to a germination medium to grow a grape plantlet.

In other preferred embodiments of the eighth aspect, the plant growth regulator is an auxin, NOA, BA, zeatin, dicamba, picloram, NAA, IAA, 2,4-D, a cytokinin, thidiazuron, ABA, or GA. In yet other preferred embodiments, the liquid cell culture of step (a) is subcultured, and the recovery of the grape cell or grape cell cluster from the cellular suspension culture includes filtration, sedimentation, or selection. In other preferred embodiments, the second liquid culture medium fuirther includes a plant growth regulator (e.g., a cytokinin). The liquid cell culture of step (c) can be sieved to synchronize the formation of differentiated somatic grape embryos. If desired, the somatic grape embryo or embryogenic cell of step (a) can each be transformed with DNA. The embryogenic cell or embryogenic cell mass recovered in step (b) may also be transformed with DNA. Similarly, the recovered somatic embryo may transformed with DNA.

In a ninth aspect, the invention features a method of producing a somatic grape embryo using a solid culture medium from a perennial grape embryogenic culture. The method includes the steps of: (a) culturing a embryogenic cell in a first liquid culture medium to grow a cellular suspension culture, the first liquid culture medium including a plant growth regulator; (b) recovering an embryogenic cell or embryogenic cell mass from the cellular suspension culture; and (c) culturing the embryogenic cell or embryogenic cell mass from the cellular suspension culture of step (b) in a solid culture medium to produce a somatic grape embryo.

In preferred embodiments of the ninth aspect, the solid culture medium further includes a plant growth regulator (e.g., a cytokinin, ABA, or GA). In other preferred embodiments, the recovered embryogenic cell or embryogenic cell mass are sieved to synchronize the formation of mature somatic grape embryos.

In a tenth aspect, the invention features a method of selecting for a somatic grape embryo having resistance to a plant pathogen using a liquid culture medium. The method including the steps of: (a) culturing a somatic grape embryo in a first liquid culture medium to grow a cellular suspension culture, the first liquid culture medium including a plant growth regulator and a filtrate from a plant pathogen culture; (b) recovering an embryogenic cell or embryogenic cell mass from the cellular suspension culture; and (c) culturing the embryogenic cell or embryogenic cell mass in a second liquid culture medium to produce a somatic grape embryo.

In an eleventh aspect, the invention features a method for producing a grape plant having resistance to a plant pathogen. The method includes the general steps of: (a) culturing a somatic grape embryo in a first liquid culture medium to grow a cellular suspension culture, the first liquid culture medium including a plant growth regulator and a filtrate from a plant pathogen culture; (b) recovering an embryogenic cell or embryogenic cell mass from the cellular suspension culture; (c) culturing the grape cell or grape cell cluster in a second liquid culture medium to produce a grape somatic embryo; (d) recovering the somatic grape embryo, wherein the somatic grape embryo has resistance to the plant pathogen; and (e) growing a plant from the somatic grape embryo.

In preferred embodiments of the tenth or eleventh aspect, the method further includes transferring the somatic grape embryo to a germination medium to grow a grape plantlet. In other preferred embodiments, the pathogen filtrate is obtained from a virus, nematode, insect, fungus (e.g., *Elsinoë ampelina*), or bacterium. In other preferred embodiments, the plant growth regulator of step (a) is an auxin. In yet other preferred embodiments, the second liquid culture medium further includes a plant growth regulator.

Other features and advantages of the invention will be apparent from the following detailed description, and from the claims.

DETAILED DESCRIPTION OF THE INVENTION

Figure 1A:
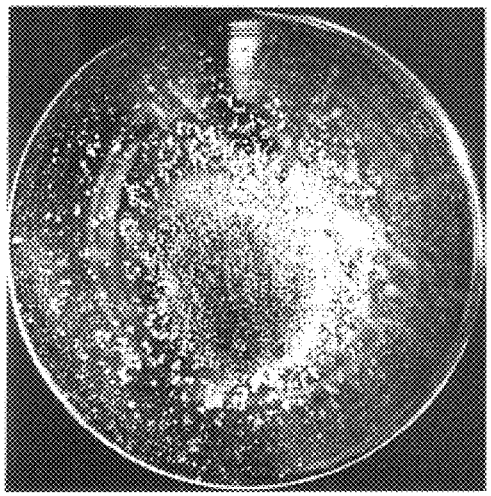
FIG. 1A is a photograph of a plant culture plate showing the embryogenic mass of 'Chardonnay' obtained from a liquid culture medium. This photograph was taken approximately ten weeks after the initiation of a liquid cell culture.

We have developed a method for growing perennial grape embryogenic cultures that is useful for the regeneration of grapes. The unique germplasm resulting from our culture system has been observed to produce grape plants with an enhanced ability to recreate embryogenic cultures. Furthermore, we have developed a process for growing large quantities of somatic grape embryos from such perennial embryogenic cultures in a relatively short period using a liquid suspension culture.

Terms used herein are defined as follows:

By "perennial grape embryogenic culture" is meant an embryogenic culture in which embryogenic cells or cell masses have been repeatedly selected, subcultured, and maintained as an in vitro culture. Such perennial grape embryogenic cultures are maintained for at least half a year, preferably three years, and most preferably four or more years.

By "embryogenic cell," "embryogenic cell mass," or "embryogenic cultures" is meant a cell or collection of cells having the inherent potential to develop into a somatic embryo and, ultimately, into a plant. Typically such cells have large nuclei and dense cytoplasm. Additionally, such cells are totipotent in that they possess all of the genetic and structural potential to ultimately become a whole plant.

By "increased level of embryogenesis" is meant a greater capacity to produce an embryogenic cell or embryogenic cell mass in a perennial grape embryogenic culture than the level of a control non-perennial grape embryogenic culture. In general, such an increased level of embryogenesis is at least 20%, preferably 50%, more preferably 100% and most preferably 250% or greater than the level of a control embryogenic culture. The level of embryogenesis is measured using conventional methods.

By "explant" is meant an organ, tissue, or cell derived from a plant and cultured in vitro for the purpose of initiating a plant cell culture or a plant tissue culture. For example, explant grape tissue may be obtained from virtually any part of the grapevine including, without limitation, anthers, ovaries, ovules, floral tissue, vegetative tissue, tendrils, leaves, roots, nucellar tissue, stems, seeds, protoplasts, pericycle, apical meristem tissue, embryogenic tissue, somatic embryos, and zygotic embryos.

By "plant growth regulator" is meant a compound that affects plant cell growth and division. Preferred plant growth regulators include natural or synthetic auxins or cytokinins. Exemplary auxins include, but are not limited to, NOA, 2,4-D, NAA, IAA, dicamba, and picloram. Exemplary cytokinins include, but are not limited to, BA and zeatin.

By "somatic embryogenesis" is meant the process of initiation and development of embryos in vitro from plant cells and tissues absent sexual reproduction.

By "somatic embryo" is meant an embryo formed in vitro from somatic cells or embryogenic cells by mitotic cell division.

By "mature somatic embryo" is meant a fully-developed embryo with evidence of root and shoot apices and exhibiting a bipolar structure. Preferred mature somatic embryos are those with well-defined cotyledons.

By "plantlet" is meant a small germinating plant derived from a somatic embryo.

By "regeneration" is meant the production of an organ, embryo, or whole plant in plant tissue culture.

By "pathogen" is meant an organism whose infection of viable plant tissue elicits a disease response in the plant tissue. Such pathogens include, without limitation, bacteria, mycoplasmas, fungi, insects, nematodes, viruses, and viroids. Plant diseases caused by these pathogens are described in Chapters 11–16 of Agrios, Plant Pathology, 3rd ed., Academic Press, Inc., New York, 1988. Examples of bacterial pathogens include, without limitation, *Agrobacterium vitis, Agrobacterium tumefaciens, Xylella fastidosa,* and *Xanthomonas ampelina*. Examples of fingal pathogens include, without limitation, *Uncinula necator, Plasmopara viticola, Botrytis cinerea, Guignardia bidwellii, Phomophsis viticola, Elsinoë ampelina, Eutypa lata, Armillaria mellea,* and *Verticllium dahliae*. Examples of pathogenic nematodes include, without limitation, root-knot nematodes (for example, Meloidogyne sp.), cyst nematodes (for example, Heterodera sp), root-attacking nematodes (for example, *Rotylenchulus reniformis*), and above-ground nematodes (for example, *Anguina funesta*). Examples of pathogenic pests (e.g., insects) include, without limitation, Phylloxera, Coleoptera, Lepidoptera, Homoptera, Dermptera, and Diptera. Examples of viral pathogens include, without limitation, grapevine fanleaf virus and grapevine leafroll virus.

By "increased level of resistance" is meant a greater level of resistance or tolerance to a disease-causing pathogen or pest in a resistant grapevine (or scion, rootstock, cell, or seed thereof) than the level of resistance or tolerance or both relative to a control plant (i.e., a grapevine that has not been subjected to in vitro selection to any plant pathogen or toxin-containing filtrate thereof). In preferred embodiments, the level of resistance in a resistant plant of the invention is at least 5–10% (and preferably 30% or 40%) greater than the resistance of a control plant. In other preferred embodiments, the level of resistance to a disease-causing pathogen is 50% greater, 60% greater, and more preferably even 75% or 90% greater than the level of resistance of a control plant; with up to 100% above the level of resistance as compared to the level of resistance of a control plant being most preferred. The level of resistance or tolerance is measured using conventional methods. For example, the level of resistance to a pathogen may be determined by comparing physical features and characteristics (for example, plant height and weight, or by comparing disease symptoms, for example, delayed lesion development, reduced lesion size, leaf wilting, shriveling, and curling, decay of fruit clusters, water-soaked spots, leaf scorching and marginal burning, and discoloration of cells) of resistant grape plants with control grape plants.

By "transformed" is meant any cell which includes a nucleic acid molecule (for example, a DNA sequence) which is inserted by artifice into a cell and becomes part of the genome of the organism (in either an integrated or extrachromosomal fashion for example, a viral expression construct which includes a subgenomic promoter) which develops from that cell. As used herein, the transformed organisms or cells are generally transformed grapevines or grapevine components and the nucleic acid molecule (for example, a transgene) is inserted by artifice into the nuclear or plastidic compartments of the plant cell.

By "transgene" is meant any piece of a nucleic acid molecule (for example, DNA) which is inserted by artifice into a cell, and becomes part of the organism integrated into the genome or maintained extrachromosomally) which develops from that cell. Such a transgene may include a gene which is partly or entirely heterologous (i.e., foreign) to the transgenic organism, or may represent a gene homologous to an endogenous gene of the organism.

The regeneration methods described herein have been used for the successful regeneration by somatic embryogenesis of a variety of grapevine rootstock and scion cultivars, including Autumnu Seedless, Blanc du Bois, Cabernet Franc, Cabernet Sauvignon, Chardonnay (e.g., CH 01 and CH 02), Dolcetto, Merlot, Pinot Noir (e.g., PN and PN Dijon), Semillon, White Riesling, Lambrusco, Stover, Thompson Seedless, Niagrara Seedless, Seval Blanc, Zinfindel, *Vitis rupestris* St. George, *Vitis rotundifolia* Carlos, *Vitis rotundifolia* Dixie, *Vitis rotundifolia* Fry, and *Vitis rotundifolia* Welder.

Using plant tissue culture methods described herein, we have also developed in vitro selection methods which enable those skilled in the art to develop plant-resistant grapevines. One such application is the selection of mutations in grape cell cultures. In this application, cells that are resistant or susceptible to a particular condition are selected based on increased or selective growth. The cells can further be exposed to a mutagen that results in changes in the DNA of the exposed cells. The mutagenized DNA can then be identified using standard techniques. A second, related application is the selection of pathogen-resistant cells. Cells are cultured in the presence of a pathogen. Cells that show resistance can then be used to regenerate a pathogen-resistant plant. A third application is the transfer of genetic information into grape cells. The genetic information can include nucleic acid sequence encoding a selectable marker. Culturing cells in the presence of the selective pressure results in the proliferation or survival only of the cells that have the desired genetic information. The methods described herein also enable those skilled in the art to develop, select, and propagate grape variants having novel or useful characteristics.

The methods of the invention are generally applicable for a variety of grape plants (for example, Vitis spp., Vitis spp. hybrids, and all members of the subgenera Euvitis and Muscadinia), including scion or rootstock cultivars. Exemplary scion cultivars include, without limitation, those which are referred to as table or raisin grapes Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay (e.g., CH 01, CH 02, CH Dijon), Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars include Couderc 1202, Couderc 1613, Couderc 1616, Couderc 3309 (*Vitis riparia* X *nrupestris*), Dog Ridge, Foex 33 EM, Freedom, Ganzin 1 (AxR #1), Harmony, Kober 5BB, LN33, Millardet & de Grasset 41B (*Vitis vinifera* X *berlandieri*), Millardet & de Grasset 420A, Millardet & de Grasset 101–14 (*Vitis riparia* X *rupestris*), Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris Constantia, Vitis california,* and *Vitis girdiana, Vitis rotundifolia, Vitis rotundifolia* Carlos, Teleki 5C (*Vitis berlandieri* X *riparia*), 5BB Teleki (selection Kober, *Vitis berlandieri* X *riparia*), $SO_4$ (*Vitis berlandieri* X *rupestris*), and 039–16 (*Vitis vinifera* X *Muscadinia*).

There now follows a description for each of the aforementioned methods. These examples are provided for the purpose of illustrating the invention, and should not be construed as limiting.

Perennial Grape Embryonic Culture System

The following method has proven effective for the production of perennial embryogenic grape cultures, and for the regeneration of grapevine by somatic embryogenesis.

Explant Tissue and Culture Initiation

In the culture initiation step, explant material was collected from the field, greenhouse, or in vitro shoot micropropagation cultures of grapevine and placed into in vitro culture. This explant material was typically collected from leaves, anthers, or tendrils, but is also obtained from other vegetative or reproductive tissues of grapevine. Once collected, the explant tissue, if desired, was surfaced sterilized according to standard methods, and then placed on a suitable solid culture initiation medium in a petri plate.

Any of a number of well known media, e.g., Murashige and Skoog (MS) and Nitsch's medium, may be used. Such media typically include inorganic salts, vitamins, micronutrients, a nitrogen source, and a carbon source such as sucrose, maltose, glucose, glycerol, inositol, and the like. For example, sucrose may be added at a concentration of between about 1 g/L to about 200 g/L; and preferably at a concentration of between about 30 g/L to about 90 g/L. Moreover, the composition of such plant tissue culture media may be modified to optimize the growth of the particular plant cell employed. For example, the culture initiation medium may be prepared from any of the basal media found Table 1.

TABLE 1

COMPOSITION OF MEDIA COMMONLY USED IN THE EXAMPLES

| Component (mg/L unless otherwise specified) | MS | Modified MS | Nitsch |
|---|---|---|---|
| $KNO_3$ | 1900.0 | 3033.3 | 950.0 |
| $NH_4NO_3$ | 1650.0 | — | 720.0 |
| $NH_4Cl$ | — | 363.7 | — |
| $MgSO_4 \cdot 7H_2O$ | 370.0 | 370.0 | 185.0 |
| $CaCl_2$ | 440.0 | 440.0 | 166.0 |
| $KH_2PO_4$ | 170.0 | 170.0 | 68.0 |
| $Na_2EDTA$ | 37.23 | 37.23 | 37.3 |
| $FeSO_4 \cdot 7H_2O$ | 27.95 | 27.95 | 27.95 |
| $MnSO_4 \cdot H_2O$ | 16.9 | 16.9 | 18.9 |

TABLE 1-continued

COMPOSITION OF MEDIA COMMONLY USED IN THE EXAMPLES

| Component (mg/L unless otherwise specified) | MS | Modified MS | Nitsch |
|---|---|---|---|
| KI | 0.83 | 0.83 | — |
| $H_3BO_3$ | 6.2 | 6.2 | 10.0 |
| $ZnSO_4 \cdot 7H_2O$ | 8.6 | 8.6 | 10.0 |
| $Na_2MoO_4 \cdot 2H_2O$ | 0.25 | 0.25 | 0.25 |
| $CuSO_4 \cdot 5H_2O$ | 0.025 | 0.025 | 0.025 |
| $CoCl_2 \cdot 6H_2O$ | 0.025 | 0.025 | 0.025 |
| Glycine | 2.0 | 2.0 | — |
| Nicotinic acid | 0.5 | 0.5 | 1.0 |
| Pyridoxin HCl | 0.5 | 0.5 | 1.0 |
| Thiamine HCl | 0.1 | 0.1 | 1.0 |
| Inositol | 0.1 g/L | 1.0 g/L | 0.1 g/L |
| Sucrose | 30.0 g/L; 60.0 g/L | 30.0 g/L; 60.0 g/L; 90.0 g/L | 20.0 g/L |
| Activated Charcoal | — | 0.5 g/L; 1.0 g/L; 2.0 g/L | — |
| Agar | 7.0 g/L | 7.0 g/L | 8.0 g/L |
| pH | 5.5 | 5.5 | 5.5 |

If desired, the initiation medium may contain an auxin or a mixture of auxins at a oncentration of about 0.01 mg/L to about 100 mg/L, depending on the cultivar of nterest, which is effective for inducing the production of embryogenic cells or embryogenic cell masses on the explant tissue. For example, explant tissue can be maintained on an agar-solidified Nitsch's-type medium supplemented with, e.g., between about 0.01 mg/L and about 10 mg/L of 2,4-D, and preferably between about 0.5 mg/L and about 3.0 mg/L of 2,4-D. 2,4-D is just one example of an auxin which is useful in the methods of the invention. Other auxins include, for example, NAA, NOA, IAA, dicamba, and picloram. Additionally, if desired, other plant growth regulators may be included in the medium at standard concentrations. For example, cytokinins (e.g., a naturally-occurring or synthetic cytokinin, such as BA or zeatin), if present, may be used at a concentration of from about 0.01 mg/L to about 10 mg/L, and preferably about 0.3 mg/L, depending on the cultivar of interest. In some instances, other classes of growth regulators, such as ABA or GA, may be included at appropriate standard concentrations. For example, ABA may be added at a concentration of about 0.5 mg/L to about 20 mg/L, and preferably at a concentration of about 5 mg/L; and GA may be added at a concentration of about 0.1 mg/L to about 30 mg/L, and preferably at a concentration of about 5 mg/L. The addition of plant growth regulators at this stage is not necessary for the induction of embryogenesis. Additionally, the initiation medium may also include activated charcoal (0.1–2.0 g/L) or a similar adsorbent known to those in the art.

Culturing of explant tissue during this stage is preferably carried out in the dark at 22–30° C., although it may also be carried out under very low light conditions, or in full light. After approximately one to four weeks in culture, explant tissue cultures are then placed in fall light with a 16 hr photoperiod. Cultures are scanned weekly for the presence of emerging embryogenic cells or embryogenic cell masses. Embryogenic cells or cell masses are identified based on morphology. Embryogenic cell masses, in general, tend to be white to pale yellow in color, and are often hyaline. They may be recognized from a very early, small stage (10–20 cell aggregates), based upon their color and friable, granular appearance. Embryogenic cultures are also identified by their compact nature with cells that are rich in cytoplasm (as seen under the microscope). The embryogenic cultures appear at varying frequencies depending on a multitude of factors including, but not limited to, genotype, nature and type of explant, medium composition, and season of harvest. Careful visual selection to ensure transfer of appropriate embryo-like structures is required for culture maintenance. Once identified, embryogenic cells or cell masses are then transferred to culture maintenance medium, as described herein.

Culture Maintenance

Embryogenic cells or embryogenic cell masses are carefully removed and transferred to a culture maintenance medium. Again, any of a number of well known media, e.g., MS and Nitsch's medium, may be used. Although not generally required, plant growth regulators may be added as described above.

In general, embryogenic tissue can be maintained by subculturing at regular intervals (e.g., every one to four weeks, or every four to eight weeks) to new maintenance medium, as described herein. Alternatively, embryogenic tissue can be placed in a liquid culture medium (e.g., MS, B-5, or Nitsch) and grown as a liquid embryogenic suspension as described herein. Embryogenic cell masses are grown to increase embryogenic cell biomass as required by division of expanding cultures during transfer. The cultures can be prompted to develop toward increasing embryogenesis or toward less embryogenesis and more unorganized embryogenic cell growth by repeated manipulation of the culture, which includes careful selection of embryogenic cells and cell masses during transfer. Repeated transfer of embyogenic cells or cell masses has not only been found to enrich the growth of embryogenic tissue, but also to facilitate the process of somatic embryogensis. The cultures are perennial in that they typically persist for over two years.

A key component of the present approach involves the careful selection of embryogenic cells from explanted tissue, followed by recurrent selection and subculturing of the selected embryogenic tissue. This material has not only been found to be useful in the regeneration of whole grape plants from somatic embryos, but has also been found to have a significantly increased capacity for embryogenesis, including the production of somatic embryos. By carrying out this procedure, the growth of embryogenic cells is enriched, speeding the process of somatic embryo formation and subsequent plant regeneration.

The explant material taken from plants that were grown from somatic embryos was observed to exhibit an enhanced embryogenic potential, when compared to explant material taken from clonal explant tissue which had not been cultured for the production of embryogenic cells. This increase in embryogenic potential was observed to increase after two or more successive initiation, culture and plant regeneration cycles (e.g., clonal plant→explant→embryogenic culture initiation→somatic embryo→somatic embryo-derived plant→explant). It is not necessary to use a somatic embryo-derived plant as the source of the explant; somatic embryos or even embryogenic cultures that have been transferred to new medium will also produce new somatic embryos with increased embryogenic potential. Such explant material is conveniently maintained as in vitro axillary shoot cultures, which serves as the source for vegetative explants; however, other methods of plant maintenance are also acceptable.

Germination and Plantlet Growth

Somatic embryos obtained from the above-described cultures are subsequently germinated into grape plantlets according to standard methods. For example, somatic embryos are placed on the surface of a germination medium (e.g., MS medium) in sterile petri plates. The cultures containing the embryos are incubated in a growth chamber under lighted conditions (16 hr photoperiod). During germination the root emerges and the epicotyl begins to grow. When grape plantlets that are grown on germination medium reach sufficient size (1 cm, with at least two leaves), they can be removed from the culture dishes and planted in a sterilized potting mixture. Plantlets are typically transferred into nursery containers in a soiless potting mix (e.g., Vermiculite, Perlite, or ProMix™, V.J. Growers, Apopka, Fla.). If desired, plantlets can be placed in a growth chamber or in a greenhouse moisture chamber and incubated under high humidity conditions (90% humidity) for plantlet growth and acclimatization. Subsequently, acclimatized plantlets can be transferred outdoors to a vineyard or to a greenhouse.

In one example, we describe the production of an embryogenic perennial culture of Vitis vinifera cv. "Thompson Seedless." Mother plant-derived cultures were obtained from a leaf that was surface-disinfected and inoculated onto culture initiation medium described by Nitsch (1968) and modified by Gray D. J. ("Somatic Embryogenesis in Grape." In: Somatic embryogenesis in woody perennials, Vol. 2, Gupta P. K., Jain S. M., and Newton R. J. (Eds.), Kluwer Academic, Dordrecht, The Netherlands, pp. 191–217, 1995). This medium contained about 1.1 mg/L of 2,4-D and about 0.05 mg/L of BA. After explanting the tissue, the culture vessels were incubated in complete darkness for six weeks. Most of the explanted tissue was observed to form a mass of undifferentiated, highly vacuolated cells within this six week period. Embryogenic cultures, identified by their compact nature and the presence of cells that were rich in cytoplasm, were repeatedly subcultured. The resulting culture was obtained by the selection method described above, followed by subculturing (for about 6 weeks) until enough embryogenic culture was available. A somatic embryo originally obtained from the mother plant (i.e., $1^{st}$ generation embryo) was germinated, and its shoot tip used to create an in vitro micropropagation culture. Leaves from the plant derived from that culture were then used to produce a new embryogenic culture ($2^{nd}$ generation). A somatic embryo obtained from that culture was similarly used to create the third generation. The embryogenic response of Vitis vinifera cv. "Thompson Seedless" from in vitro micropropagation culture-derived leaves is presented in Table 2 (below). These results show the comparison of leaves from potted mother plant-derived cultures with leaves from plants derived from cultures obtained from third-generation germinated somatic embryos.

TABLE 2

| Culture derivation | No. leaves cultured | No. embryogenic cultures | % response per leaf |
|---|---|---|---|
| Mother plant | 195 | 0* | 0 |
| $3^{rd}$ generation somatic embryo | 200 | 14 | 7# |

*Other experiments have yielded one embryogenic culture.
The percent response per leaf has been found to be has high as 30%.

In addition, perennial embryogenic cultures from other grapevines have also been produced using the methods described herein, including Vitis Jongii, Vitis rotundifolia (cv. Carlo and Dixie), Vitis rupestris, Vitis vinifera (cv. Autumn Seedless, Cabernet Sauvignon, Cabernet Franc, Chardonnay, Dolcetto, Gamay Beaujolais, Lambrusco, Pinot Noir, Semillon, Tokay, White Riesling, Zinfindel, and the like), and several Vitis hybrids (cv. Blanc du Bois, Niagara Seedless, Seyval Blanc, Stover, Southern Home and the like).

Production of Highly Embryogenic Grape Cells Using a Liquid Suspension or Solid Cultures A method has also been developed for the production of large quantities of grapevine somatic embryos using either a liquid cell suspension culture or a solid culture system. These methods are particulary useful for producing highly embryogenic cells that are capable of regenerating into whole plants. Below, a simple protocol for efficient somatic embryogenesis of grapevine using either a liquid cell suspension culture or a solid culture system is presented.

In general, the method includes a multistage culturing process typically involving (i) culture initiation; (ii) identification and isolation of embryogenic cells or embryogenic cell masses; (iii) production of perennial embryogenic cultures; and (iv) concentration of highly embryogenic cell clusters. The method involves the following steps.

Explant tissue is placed on a suitable culture initiation medium, as is described herein. After approximately six weeks on culture initiation medium, embryogenic cells and embryogenic cell masses are identified. Once identified, embryogenic cultures, which may be less than 1 mm in diameter, are isolated and cultured on fresh initiation medium to encourage growth, as described herein. Subculturing of the embryogenic cultures typically results in the formation of somatic embryos. Embryogenic cultures and early stage somatic embryos obtained from these cultures are then further cultured in a suitable liquid plant growth medium. For example, the plant tissue culture nutrient media, consisting B-5 medium (Gamborg et al, Exp. Cell. Res. 50:151–158, 1968; Sigma Chemicals, St. Louis, Mo.), that has been modified as described by DeWald et al. (J. Amer. Soc. Hort. Sci. 114:712–716, 1989) and Litz et al. ("Somatic embryogenesis in mango," 1995, supra). This modified medium consists of B-5 major salts, MS minor salts and vitamins, glutamine (about 400 mg/L), and sucrose or commercial table sugar (about 60 g/L). Before autoclaving, the pH of the medium is adjusted to about 5.8. Although 2,4-D (about 0.5–2.0 mg/L) is the preferred growth regulator used in this medium, other growth regulators, such as, for example, dicamba, picloram, NOA, or 2,4,5-trichlorophenoxyacetic acid, may be also used at appropriate concentrations, for example, those described above. Flasks containing the embryogenic cell cultures, somatic embryos, or both are subsequently incubated at about 26° C. on a rotary shaker at 125 rpm in darkness or diffuse light. The cultures are then subcultured as described herein, typically once every ten to fourteen days, but subculturing regimens may vary depending on the growth and proliferation of embryogenic cell clusters.

In about six to eight weeks, a fine cell suspension culture is produced, which consists of highly-vacuolated elongated cells (non-embryogenic cells), and also a lesser number of small, cytoplasm-rich, isodiametric cells (embryogenic cells). Once sufficient culture is produced, the differentiated embryos can be removed from the culture by sieving, and the differentiated embryos are discarded. Continued maintenance of the sieved embryogenic cell suspension culture in modified B-5 liquid medium, with periodic subcultures, has been found to increase the biomass of embryogenic cell clusters.

After approximately twelve to sixteen weeks, a large mass of highly concentrated embryogenic grape cells is typically observed. The time taken for the concentration of embryogenic cells or embryogenic cell masses may vary depending on several factors, including the cultivar, genotype, and culture conditions. Embryogenic cells at this stage are especially useful in virtually any type of genetic transformation method. These embryogenic cells can also be induced to differentiate into somatic embryos according to any standard method, e.g., by culturing the cells in modified B-5 liquid medium devoid of growth regulators for a period of about four to six weeks. Alternatively, the early stage somatic embryos may be plated in medium solidified by the addition of a suitable gelling agent such as gellan gum, agarose, agar, or any other similar agent, for further differentiation of somatic embryos in complete darkness. If desired, torpedo/cotyledonary-stage embryos can be individually subcultured on a standard maturation medium, e.g., a maturation medium consisting of MS nutrient formulations. Mature somatic embryos are then transferred to a growth chamber for germination, and regeneration to plants in an appropriate container. The frequency of somatic embryo formation using this procedure is typically high.

There now follows a description of the results for the production of embryogenic cells and cell masses obtained from a liquid suspension and solid cultures of "Thompson Seedless" and two different clones of Chardonnay, CH 01 and CH 02.

Asynchronous somatic embryos of *Vitis vinifera* cv. "Thompson Seedless" and Chardonnay CH 01 and CH 02 obtained from perennial embryogenic tissue were further cultured in a liquid medium to produce a callus tissue suspension culture. After about fourteen days and following about two to three subcultures (a subculture was performed about every fourteen days), an amorphous, yellowish to creamy white colored callus was produced. As a result of the production of callus tissue, the liquid culture media in the tissue culture flask appeared as a dense suspension. Microscopic examination revealed that the callus cells were elongated and highly vacuolated, and exhibited no signs of embryogenic capacity. Amorphous callus continued to proliferate, even when the somatic embryos used to initiate the culture were removed from the culture.

After approximately six weeks in modified B-5 liquid medium, we observed the production of small clusters of cytoplasm-rich cells as white clumps (FIG. 1A). These embryogenic masses were observed to proliferate exponentially, and grew to the capacity of the flask in about ten to twelve weeks.

Continued maintenance of these embryogenic masses as a single unit (i.e., in one flask) is often detrimental, as the cultures have been found to deteriorate in quality, and eventually turn brown. Dividing these embryogenic cultures into smaller units during subculturing assists to proliferate and increase the biomass of the divided cultures. Among the two cultivars tested, both clones of "Chardonnay" were found to be equally fast growing and outgrew "Thompson Seedless." While the embryogenic masses of "Chardonnay" were creamy white to yellowish in color, those of "Thompson Seedless" were dull white or brownish. In addition, "Thompson Seedless" appeared to be more sensitive to culture density, as the cells were observed to turn dark if the culture density was not corrected. The preferred culture density was approximately 400 mg of embryogenic cells per 40 mL of liquid modified B5 medium in a 125 mL flask.

Somatic Embryo Production in Liquid Culture

Embryogenic masses were passed through a 960 micron nylon sieve and collected in a sterile beaker. Sieving of the embryogenic masses to initiate embryogenesis in liquid culture was found to serve two purposes. First, a fair degree of synchronization of embryo differentiation was obtained. Second, the formation of somatic embryo abnormalities during differentiation, such as fasciation or fuision, was reduced. After four to six weeks in liquid medium, small, white somatic embryos in the globular or early heart stage were observed. Sieving the cultures at this stage did not facilitate an increase in embryo differentiation.

After approximately eight weeks, somatic embryos were clearly visible, and a few embryos were found to have reached the cotyledonary stage of embryo development. Sieving the differentiated embryos and culturing them in a separate flask, however, facilitated faster differentiation, as well as synchronization of embryo devlopment.

Figure 1B:
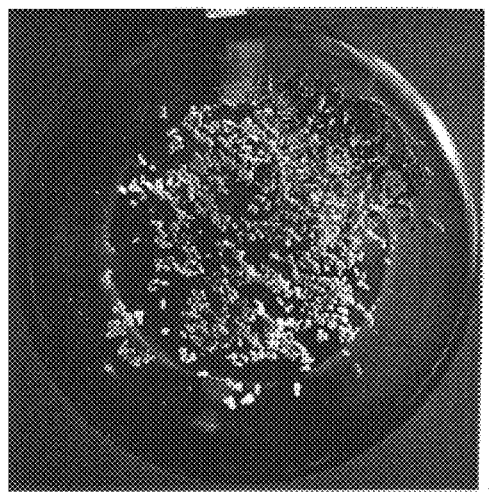
FIG. 1B is a photograph of a plant culture plate showing cotyledonary stage somatic embryos. This photograph was taken approximately twelve weeks after the initiation of embryo development.
Figure 1C:
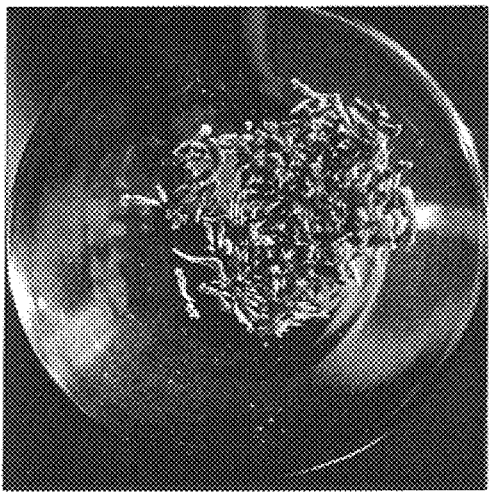
FIG. 1C is a photograph of a plant culture plate showing mature somatic embryos starting to precociously germinate in liquid culture. Note the elongation of roots in many embryos. This photograph was taken approximately twenty weeks after the initiation of embryo development.

Both "Chardonnay" clones—CH 01 and CH 02—were found to readily differentiate into somatic embryos. Appropriate sieving and density adjustment (performed by culturing about 1000 mg of somatic embryos per 40 mL medium) ensured greater synchronization and singulation, as well as embryo differentiation (FIG. 1B). In approximately twelve to fourteen weeks after subculture in liquid embryogenesis medium, singulated somatic embryos started to turn green and radicles elongated, showing the onset of precocious germination (FIG. 1C).

Cultures of "Thompson Seedless" initially were found not to advance beyond the heart stage in liquid culture. In addition, the embryos were found to be more clustered, often resulting in the formation of fused somatic embryos. Removal of the abnormal embryos and lowering the culture density by half resulted in normal somatic embryogenesis in liquid culture. These somatic embryos reached maturity in about fourteen to eighteen weeks.

Somatic Embryo Production in Solid Medium

Figure 1D:
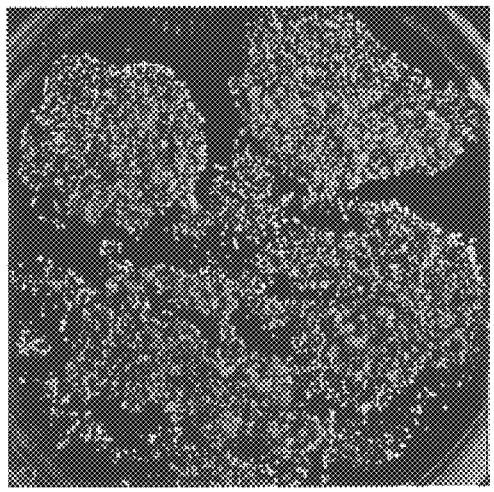
FIG. 1D is a photograph of a plant culture plate showing initial stages of somatic embryo differentiation in a solid medium after five weeks of culturing. These somatic embryos were obtained from embryogenic cell masses that were cultured in a liquid medium (from FIG. 1A).
Figure 1E:
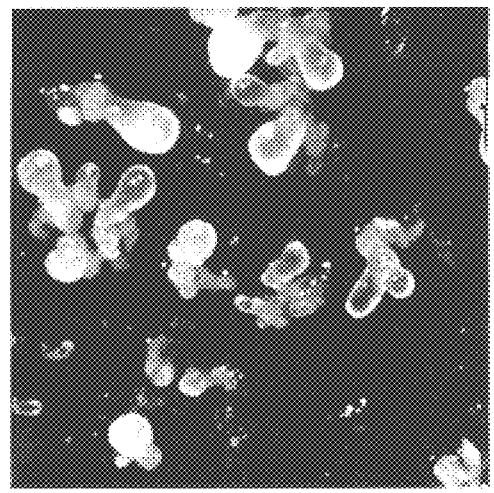
FIG. 1E is a photograph of a plant culture plate showing the early stages of somatic embryo development in a solid medium. Very early somatic embryos are hyaline and start turning opaque after a few days.
Figure 1F:
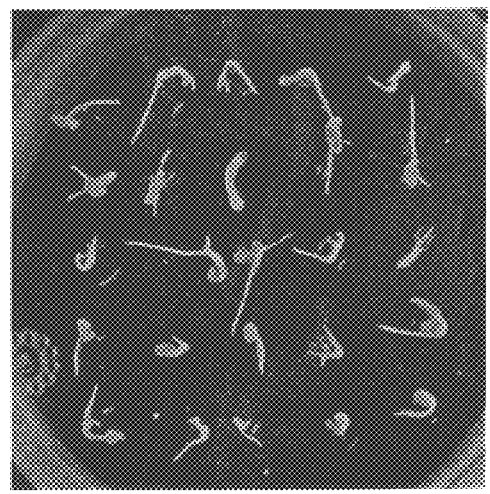
FIG. 1F is a photograph of a plant culture plate showing mature somatic embryos germinating on a MS basal medium with 3% sucrose.

Embryogenic cells or embryogenic cell masses obtained from liquid cultures were observed to differentiate into somatic embryos as early as three weeks after culture initiation. After four weeks of culture, microscopic examination also revealed the formation of globular and heart shaped somatic embryos on the callus tissue (FIG. 1D). The somatic embryos were hyaline, and resembled that of a hyperhydric state (FIG. 1E); however, the embryos continued to differentiate, and were found to develop into mature somatic embryos in another three to four weeks. These somatic embryos were observed to develop a suspensor (FIG. 1E). In addition, embryogenic cells were observed to develop into a mass of asynchronous somatic embryos.

One of the interesting observations from these experiments was that the majority of somatic embryos arose as individual units, and not as small clumps, although there were a few clumps of somatic embryos. In such cases, the number of somatic embryos ranged from six to ten in each clump, and these embryos were easily separated from the callus tissue. Embryos found in the cotyledonary stage were isolated on a weekly basis, and subcultured for maturation. Each clump of embryogenic mass continued producing somatic embryos for at least twelve weeks. Embryogenic cell masses tended to turn brown in solid medium, containing Gel-Gro (ICN Biochemicals), but this discoloration did not adversely affect culture viability. About four or five weeks later, clusters of somatic embryos started to appear on the surface of the brown embryogenic cells or embryogenic cell masses.

Somatic Embryo Maturation, Germination and Plant Regeneration

Three maturation media—mango maturation medium (Litz et al., "Somatic embryogenesis in mango," 1995, supra); mango maturation medium solidified with agar (7 g/L); and MS basal medium with 3% sucrose—were studied to evaluate the ability to promote somatic embryo germination and plant regeneration. Our results indicated that a MS basal medium containing 3% sucrose was the most effective at promoting embryo maturation, germination, and plant regeneration, for both embryos derived from solid medium and for the precociously germinated embryos that were obtained from liquid medium cultures (FIG. 1D). Although there was good germination on mango maturation medium with agar, the quality of the regenerants was not as good as with MS salts with 3% sucrose. Embryos from the two systems studied (i.e., liquid and solid media) showed variation between themselves in germination and regeneration. Although embryos have precociously germinated in liquid cultures, continued germination in these cultures was not observed. On transfer to solid medium, however, the embryos were found to continue the germination process, and resulted in the formation of grape plants with a dense root system. Continued maintenance in liquid medium after radicle emergence lead to hyperhydricity and eventually plant regeneration was reduced from these embryos. Accordingly, it is preferred that the somatic embryos should be removed from the liquid as soon as they precociously germinate and transferred to solid medium.

Long-term Preservation of Suspension-derived Grapevine Somatic Embryos and Regeneration of Plants We have established a method for the long-term storage of somatic embryos. Mature somatic embryos from suspension cultures of "Chardonnay" were blot-dried on sterile filter paper in a laminar-flow hood and then stored in sterile petri plates at 6° C. Samples were periodically drawn from these plates and germinated on MS medium with 3% sucrose. Germination (i.e., the emergence of roots from the somatic embryo) and plant regeneration were recorded. Table 3 shows the data from clone CH 02 after 22 months in storage, and Table 4 shows the data from clone CH 01 after 5 months in storage.

TABLE 3

| Trial Number | Number of Embryos | Number Germinated (Percent Germinated) | Number of Plants | Percent Yield |
|---|---|---|---|---|
| 1 | 87 | 81 (93.1) | 69 | 79.3 |
| 2 | 42 | 40 (95.2) | 35 | 83.3 |
| 3 | 41 | 41 (100.0) | 30 | 73.2 |
| Total | 170 | 162 (95.3) | 134 | 78.8 |

TABLE 4

| Trial Number | Number of Embryos | Number Germinated (Percent Germinated) | Number of Plants | Percent Yield |
|---|---|---|---|---|
| 1 | 15 | 15 (100.0) | 13 | 86.7 |
| 2 | 15 | 15 (100.0) | 13 | 86.7 |
| 3 | 15 | 13 (86.7) | 9 | 60.0 |
| 4 | 15 | 12 (80.0) | 7 | 46.7 |
| 5 | 15 | 13 (86.7) | 9 | 60.0 |
| 6 | 15 | 11 (73.3) | 9 | 60.0 |
| 7 | 15 | 15 (100.0) | 14 | 93.3 |
| 8 | 15 | 13 (86.7) | 9 | 60.0 |
| Total | 120 | 107 (89.2) | 83 | 69.2 |

Direct Seeding of Suspension Culture-derived Grapevine Somatic Embryos

"Chardonnay" and "Thompson Seedless" grapevine somatic embryos were produced from liquid cultures as described herein. Suspension-derived, mature somatic embryos were blot dried briefly in the laminar flow hood and germinated directly in Magenta vessels containing one of the following potting media: i) sand; ii) ProMix™ commercial potting mixture (CPM); or CPM overlaid with sand. Each vessel containing 20 mL of distilled water and the potting medium was sterilized by autoclaving for 30 min and cooled overnight prior to inoculating the somatic embryos. Three somatic embryos were placed in each vessel. Seeding was carried out under aseptic conditions and the containers were closed and incubated at 26° C. with a 16 hr photoperiod at 75 $\mu$mol s$^{-1}$ m$^{-2}$ light intensity. Results revealed that CPM overlaid with sand was ideal for plant development. Although sand promoted more germination, the resulting plants were chlorotic and their survival rate was poor. There was more contamination of somatic embryos on pure CPM. The present study offers scope for large-scale multiplication of grapes using suspension cultures and sets the platform for growing grape somatic embryos in bioreactors.

The experimental results described above were carried out using the following techniques.

Culture Initiation

Embryogenic cultures were initiated from anthers and ovaries of the cultivar "Chardonnay" (Clones CH 01 and CH 02), and from the leaves of the cultivar "Thompson Seedless" according to standard methods, e.g., those described herein. Somatic embryos of these cultures, initiated and maintained in modified MS medium, were used to initiate liquid cell suspension cultures. Typically these cultures are highly asynchronous in embryonic development and differentiation and, therefore, each inoculum consisted of somatic embryos at various stages of development.

Establishment of Liquid Cultures from Differentiated Somatic Embryos

The composition of the liquid medium was adapted from the medium described by Litz et al., supra as follows. Callus induction was achieved by the addition of 1 mg/L of 2,4-D in the medium. The pH of the medium was adjusted to about 5.8, and dispensed as 40 mL aliquots in 125 mL Erlenmeyer flasks. The flasks were tightly covered with heavy duty aluminum foil before autoclaving. After cooling, approximately one gram of the somatic embryos was transferred to the liquid medium using a sterilized spatula under aseptic conditions. The neck of the flask was sealed with Parafilm, and the cultures were then incubated in semi-darkness (diffused light) on a rotary shaker at about 120 rpm. The cultures were subcultured at least one time every two weeks.

Flasks containing the suspension cultures were removed from the orbital shaker and the cultures were allowed to settle for about 15 minutes. The supernatant was gently decanted into a sterile flask, leaving the embryogenic cells in a minimal volume (approximately 5 mL). Approximately 35 mL of fresh liquid medium was added to the embryogenic cells and swirled quickly. The entire contents of the flask were then transferred to a sterile 125 mL flask. This second flask, containing the embryogenic cells, was then sealed with Parafilm and returned to the orbital shaker.

The amorphous callus generated from the somatic embryos was collected as follows. The embryogenic suspension, including differentiated somatic embryos and callus, was allowed to settle in the flasks. About half of the supernatant medium was decanted, and the remainder was swirled and quickly filtered through a presterilized, nylon mesh (960 microns), placed over a 150 mL beaker. While the differentiated somatic embryos were retained in the mesh, the fine callus that passed through along with the liquid medium was collected in the beaker. The callus that was collected in the beaker was next filtered through a sterile, double-folded, Kimwipe placed over a sterile funnel. The amorphous callus that adhered to the Kimwipe was subsequently removed from the Kimwipe using a sterilized spatula, and resuspended in fresh liquid culture medium.

Approximately 100 mg of the callus was suspended in each flask. These liquid cultures were subcultured as described herein approximately once every fourteen days in modified B-5 liquid medium containing 2,4-D.

Somatic Embryo Production in Suspension Culture

Embryogenic cells or cell masses that were initiated in liquid suspension cultures were sieved using a 960 micron sieve, and the finer fraction was harvested in liquid embryogenesis medium, under aseptic conditions. The medium composition was the same as that of the initiation medium; however, 2,4-D was omitted from the medium and about 0.05 mg/L of BA was added. After adjusting the pH to 5.8, the medium was dispensed as 40 mL aliquots in 125 mL Erlenmeyer flasks, covered with aluminum foil and autoclaved. Approximately 100 mg of callus was cultured in each flask. The cultures were maintained in semidarkness at 25° C. on a rotary shaker at 120 rpm, and subcultured once every 14 days. Sieving of cultures was done as necessary, in order to synchronize differentiated somatic embryos. Finer mesh sieves (e.g., 520 micron sieves), if necessary, may also be employed.

Germination of Somatic Embryos from Suspension Cultures and Regeneration

Greening somatic embryos having elongated radicles were sieved from the suspension cultures. Somatic embryos were individually picked and cultured. Three different media—mango maturation medium (Litz et al., "Somatic embryogenesis in mango," 1995, supra), mango maturation medium solidified with agar (7 g/L) instead of Gel-Gro, and MS basal medium with 3% sucrose—were tested for germination and plant regeneration. Plant growth regulators were omitted from these media preparations. Twenty-five embryos were cultured in each standard petri plate, and eight plates of each medium was tested. After sealing with Parafilm, the cultures were incubated in a growth chamber under a 16 hour photoperiod. Plantlets with four true leaves were subsequently transferred to soil.

Somatic Embryo Production in Solid Medium

Embryogenic cells and embryogenic cell masses produced in suspension cultures were harvested as described above and then transferred to solid embryogenesis medium. The medium consisted of the same compounds as the liquid embryogenesis medium, and solidified with 2.0 g/L Gel-Gro or 7 g/L agar. Approximately 50 mg of callus was placed as a clump onto a medium-containing petri plate and each plate had two such clumps. After inoculating, the petri plates were sealed with Parafiln and incubated in complete darkness. Subculturing was performed after somatic embryo differentiation was observed. Somatic embryos produced from the embryogenic cells or embryogenic cell masses were counted on a weekly basis, starting from six weeks after culture. Embryos of cotyledonary stage were counted and subcultured for maturation.

Maturation and Germination of Somatic Embryos from Solid Medium

Mature somatic embryos that were approximately 5 mm in length were isolated from the asynchronous mass and cultured on maturation medium. Twenty-five mature somatic embryos were cultured in each standard petri plate on MS medium with 3% sucrose. The cultures were kept in the dark until they germinated. After elongation of radicle, they were transferred to light under a 16 hour photoperiod. Plantlets with at least four true leaves were subsequently transferred to soil.

Selection of Disease Resistant Embryogenic Cells and Plants of Grapevine

The perennial grape embryogenic cultures of the invention can be used for the selection or screening for grape cells having resistance to toxic substances, such as substances produced by plant pathogens. Such pathogens include, without limitation, bacteria, mycoplasmas, fungi, insects, nematodes, viruses, and viroids. Plant diseases caused by these pathogens are described in Chapters 11–16 of Agrios, *Plant Pathology*, 3rd ed., Academic Press, Inc., New York, 1988, hereby incorporated by reference. Examples of bacterial pathogens include, without limitation, *Agrobacterium vitis, Agrobacterium tumefaciens, Xylella fastidosa,* and *Xanthomonas ampelina*. Examples of fungal pathogens include, without limitation, *Uncinula necator, Plasmopara viticola, Botrytis cinerea, Guignardia bidwelli, Phomophsis viticola, Elsinoë ampelina, Eutypa lata, Armillaria mellea,* and *Verticllium dahliae*. Examples of pathogenic nematodes include, without limitation, root-knot nematodes (for example, Meloidogyne sp.), cyst nematodes (for example, Heterodera sp), root-attacking nematodes (for example, *Rotylenchulus reniformis*), and above-ground nematodes (for example, *Anguina funesta*). Examples of pathogenic pests (e.g., insects) include, without limitation, Phylloxera, Coleoptera, Lepidoptera, Homoptera, Dermptera, and Diptera. Examples of viral pathogens include, without limitation, grapevine fanleaf virus and grapevine leafroll virus.

By exposing embryogenic cultures to a crude culture filtrate or a purified toxin obtained from a plant pathogen, resistant grape cells can be selected and propagated. Grape cells that survive the selection pressure are expected to resist not only the selecting toxin, but also the original microbe that produces the toxin. Moreover, due to the dynamics of the selection process, induced resistance may also function against an array of disease-causing organisms beyond the original microbe used for selection. Because the selection is carried out at the cellular level, it is likely that grape plants regenerated from the cells will show the selected characteristic. In particular, this system allows one skilled in the art to select or screen for the desired characteristic from among thousands of cells in a single culture flask or petri plate.

Grapevine Diseases

Various microbes attack grapevine and cause a number of diseases. These diseases include fungal diseases of leaves and fruits (such as black rot and anthracnose), fungal diseases of the vascular system and roots (such as Esca, Black Measles, Black Dead Arm, and Eutypa dieback), bacterial diseases (such as crown gall and Pierce's disease), diseases caused by viruses and virus-like agents (such as rupestris stem pitting, grapevine leafroll, and grapevine fanleaf degeneration), as well as diseases caused by nematodes and mycoplasma.

One disease affecting grapevine is anthracnose, also known as bird's eye spot disease, which is caused by the fungus, *Elsinoë ampelina*. Under favorable conditions, this fungus attacks almost all the aerial parts of the grapevine, including fruits, causing extensive damage to the crop. Anthracnose causes the appearance of circular lesions with brown or black margins and round or angular edges on the grapevine plant. The center of the lesions becomes grayish white and eventually dries up and falls off, leaving a 'shot-hole' appearance. The disease especially affects young leaves, preventing normal development. New shoots are also affected and acquire an obvious, burnt appearance. Fruit clusters are also susceptible to fungal infection throughout their development; lesions on the berries extend into the pulp, often inducing cracking. (Pearson and Goheen, *Compendium of Grape Disease*, APS Press, St.Paul Minn., 1988).

Pathogen Filtrate

An *Elsinoë ampelina* culture filtrate having toxic activity was prepared as follows. Full-strength Czapekk-Dox broth medium (Fisher Scientific, Springfield, N.J.) was prepared by dissolving the required amount of the broth mixture in de-ionized (DI) water. The medium was dispensed as 50 mL aliquots in 125 mL Erlenmeyer flasks. After autoclaving and cooling, 100 μL of a *Elsinoë ampelina* spore suspension was added to each flask (Day 1); the flask was then incubated in a rotary shaker at 120 rpm for one week in the dark. After one week, the contents in each flask were transferred to 100 mL of full strength Czapek-Dox in a 250 mL Erlenmeyer flask and the incubation was continued for two more weeks. At the end of this period (i.e., three weeks from Day 1), the fungal culture filtrate was collected by filtering the contents of each flask through a sterile, multi-layer cheese cloth. The crude culture filtrate was stored at −40° C. until further use as previously described (Subramanian, J., "Selection and characterization of resistance in mango (*Mangifera indica* L.) embryogenic cultures to the phytotoxin produced by *Colletotrichum gloeosporioides*, Penz.," Ph.D. Dissertation, University of Florida, Gainesville, 1995).

Prior to addition to the culture media for in vitro selection, the frozen culture filtrate was thawed (without heating) at room temperature, pH adjusted to 5.8, and filter-sterilized through a 0.2 micron filter (Nalgene, Rochester, N.Y.). This filter-sterilized pathogen filtrate was found to retain its toxic activity.

Selection

The *Elsinoë ampelina* culture filtrate was next added to liquid suspension cultures of *V. vinifera* cv. "Chardonnay" embryogenic cells and embryogenic cell masses in modified B-5 medium to select cells having resistance to the toxic fungal culture filtrate. The grape embryogenic cells and embryogenic cell masses were grown as described above; however, in this in vitro selection, the medium in which the cells were grown was supplemented with known volumes of *Elsinoë ampelina* culture filtrate. Appropriate dilutions of pathogen filtrate were determined by examining the toxicity of the filtrate using serial dilution analysis. These experiments demonstrated that a 40% (v/v) culture filtrate was useful for in vitro selection.

Cultures of "Chardonnay" embryogenic cells and embryogenic cell masses were maintained in liquid medium containing 40% (v/v) fungal culture filtrate at about 26° C. on a rotary shaker (125 rpm) in diffuse light. Subculturing was done once in ten days; during each subculture, filter-sterilized culture filtrate was used to dilute the medium. Selection with culture filtrate was continued for four or five cycles (each cycle =ten days) of subculture. While most of the embryogenic cells died, a very few cells, often less than 1%, survived the selection pressure. Resistant culture lines were established by withdrawing the selection pressure after four or five cycles and letting the surviving cells grow in modified B-5 medium devoid of culture filtrate. These resistant lines were proliferated, and somatic embryo were produced using the methods described herein.

Embryogenic cell cultures obtained from the selection process were subsequently tested for resistance to *Elsinoë ampelina* using a number of in vitro bioassays. We first analyzed whether the resistant grapevine lines were producing an activity that could inhibit the growth of the fungus. To this end, the culture medium (i.e., conditioned culture medium) from a resistant culture line was tested for an inhibitory activity against the fungus. Conditioned media was collected from different cell cultures having resistance to Elisnoë, and used in several concentrations to prepare fungal growth media. An actively growing mycelial colony was placed in the center of a petri plate containing a fungal growth medium prepared with or without (control) conditioned medium from a resistant grapevine culture line and incubated under standard conditions. The results of these experiments showed that the growth of the fungus was inhibited by a fungal growth medium containing 25% or more of the conditioned medium.

To further demonstrate the presence of an anti-fungal activity in resistant grapevine cultures, resistant lines, as well as control lines, were placed in solid plant growth medium in six and twelve o'clock positions in petri plates, and incubated in darkness for four weeks. After this period, a plug of mycelium from an actively growing Elsinoë colony was placed in the center of the petri plates and incubated under standard conditions. The fungus was observed to grow rapidly and infect the control cultures. Conversely, fungal growth was inhibited on the plates containing grape cell cultures having resistance to the Elsinoë culture filtrate. Hyphae did not grow freely through the medium in plates containing these resistant cultures, as compared to fungal hyphae growth through the medium in plates containing control (i.e., non-resistant) cultures. A thick mat of mycelium, as seen in the plates containing control cultures, was never formed in the plates containing the *Elsinoë ampelina* resistant cultures. This capacity of he resistant cultures to inhibit the growth of *Elsinoë ampelina* was retained nine months after selection, demonstrating that the genetic changes in the resistant cultures were stable.

In addition, the grapevine cultures that were resistant to *Elsinoë ampelina* were tested for resistance to a second fungal pathogen, *Fusarium oxysporum*. Resistant lines, as well as control lines, were placed in solid plant growth medium in six and twelve o'clock positions in petri plates, and incubated in darkness for four weeks. After this period, a plug of mycelium from an actively growing *Fusarium oxysporum* colony was placed in the center of the petri plates and incubated at room temperature under a 16 hour photoperiod. The fungus was observed to grow rapidly and infect the control cultures. Conversely, growth of *Fusarium oxysporum* was inhibited on the plates containing grape cell cultures having resistance to the Elisnoë culture filtrate. Hyphae did not grow freely through the medium in plates containing these resistant cultures, as compared to fungal hyphae growth through the medium in plates containing control (i.e., non-resistant) cultures. A thick mat of Fusarium mycelia, as seen in the plates containing control cultures, was never formed in the plates containing the *Elsinoë ampelina* resistant cultures. This experiment demonstrated that the resistant grapevine cultures were not only resistant to *Elsinoë ampelina*, but were also resistant to *Fusarium oxysporum.*

Further analysis was made to determine if the fungal-resistant grapevine cultures could give rise to somatic embryos that were also resistant to *Elsinoë ampelina*. Somatic embryos derived from resistant cultures and control (i.e., non-resistant) control were grown either in medium containing 40% (v/v) of fungal culture filtrate or in control medium containing no fungal culture filtrate. While somatic embryos derived from the resistant cultures formed and germinated normally in both the fungal culture filtrate-containing medium and control medium, somatic embryos derived from control cultures turned necrotic and eventually died in the fungal culture filtrate-containing medium, but did not die in the control medium. The necrosis of the controls in the fungal culture filtrate-containing medium was rapid enough to turn the control somatic embryos dark within seventy-two hours of culture initiation. The results from these experiments demonstrated that the somatic embryos obtained from resistant cell cultures were also resistant to the fungal filtrate. Furthermore, these resistant somatic embryos were observed to withstand a concentration of *Elsinoë ampelina* culture filtrate that was equal to that withstood by their progenitor resistant embryogenic cells and embryogenic cell masses.

Disease-resistant Plants

Embryogenic cultures were selected in vitro against fungal culture filtrate produced by *Elsinoë ampelina*. Plants were regenerated from the selected cultures and acclimatized in the greenhouse. Plants from selected lines and unselected controls were sprayed with a spore suspension ($1 \times 10^6$ spores /mL) until runoff. The plants were individually bagged to maintain humidity (a condition is optimum for the pathogen to cause anthracnose disease) for 3 days. The bags were then removed and the plants were scored for anthracnose symptoms. All of the unselected controls exhibited a very high degree of susceptibility, and in most cases there was defoliation due to the disease within 3 days. Among the 40 different plants from the two selected lines, only one plant showed mild anthracnose symptoms. These data show that the resistance acquired by the embryogenic cells during in vitro selection can be translated into whole plant resistance against the pathogen.

Regenerated plants may be tested for resistance to anthracnose according to standard methods. For example, spore suspensions from *Elsinoë ampelina* are prepared by suspending spore masses from fresh colonies of the fungus in sterile deionized (DI) water and the spore density is adjusted to 100,000 spores/mL using a hemocytometer. Young leaves from greenhouse-grown shoots or plants are collected and washed gently with DI water. On the leaf lamina, 100 $\mu$L of the spore suspension is placed in a spot and, to facilitate inoculation of the fungus, a sharp prick is made at the center of the spot. At least two such spots are made in each leaf. The leaves are incubated in moist conditions (i.e., conditions ideal for the development of symptoms) for at least 72 hours and then observed for lesion development as previously described (Subramanian, J., Ph.D. Dissertation, University of Florida, Gainesville, 1995, supra). Similar tests with DI water alone serves as a control. In addition, leaves from cultivars that are known to be susceptible or resistant to anthracnose are inoculated and the lesions from these leaves serve as standard for assessing the susceptibility/resistance of the regenerated plants derived from in vitro selected embryogenic cells. From a statistical analysis of these data, levels of resistance to *Elsinoë ampelina* and anthracnose are determined. Grape plants having an increased level of resistance to *Elsinoë ampelina* and anthracnose or both relative to control plants are taken as being useful in the invention.

Grapevine Transformation

The method described herein can be used to produce transformed plants. Cells can be transformed at any step in the process of making a somatic embryo-derived. Thus, tissue or cells suitable for transformation include explanted tissue, embryogenic cells, embryogenic cell masses, and somatic embryos (including mature somatic embryos).

Cell cultures produced according to the methods of the invention may be transformed with DNA comprising a desired transgene. Such cells, for example, may be transformed with genes which confer resistance to pathogens, diseases, or pests, or any combination thereof. For example, a number of *Bacillus thurigiensis* genes which encode proteins that are toxic to a number of pests are well known and useful in the methods of the invention. Several standard methods are available for introduction of a transgene into a plant host, thereby generating a transgenic plant.

Upon construction of the plant expression vector, several standard methods are available for introduction of the vector into a plant host, thereby generating a transgenic plant. These methods include (1) Agrobacterium-mediated transformation (*A. tumefaciens* or *A. rhizogenes*) (see, e.g., Lichtenstein and Fuller In: *Genetic Engineering*, vol 6, PWJ Rigby, ed, London, Academic Press, 1987; and Lichtenstein, C. P., and Draper, J,. In: *DNA Cloning*, Vol II, D. M. Glover, ed, Oxford, IRI Press, 1985)); (2) the particle delivery system (see, e.g., Gordon-Kamm et al., *Plant Cell* 2:603 (1990); or BioRad Technical Bulletin 1687, supra); (3) microinjection protocols (see, e.g., Green et al., supra); (4) polyethylene glycol (PEG) procedures (see, e.g., Draper et al., *Plant Cell Physiol.* 23:451, 1982; or e.g., Zhang and Wu, *Theor. Appl. Genet.* 76:835, 1988); (5) liposome-mediated DNA uptake (see, e.g., Freeman et al., *Plant Cell Physiol.* 25:1353, 1984); (6) electroporation protocols (see, e.g., Gelvin et al., supra; Dekeyser et al., supra; Fromm et al., *Nature* 319:791, 1986; Sheen *Plant Cell* 2:1027, 1990; or Jang and Sheen *Plant Cell* 6:1665, 1994); and (7) the vortexing method (see, e.g., Kindle supra). The method of transformation is not critical to the invention. Any method which provides for efficient transformation may be employed. As newer methods are available to transform crops or other host cells, they may be directly applied.

The following is an example outlining one particular technique, an Agrobacterium-mediated plant transformation. By this technique, the general process for manipulating genes to be transferred into the genome of plant cells is carried out in two phases. First, cloning and DNA modification steps are carried out in *E. coli*, and the plasmid containing the gene construct of interest is transferred by conjugation or electroporation into Agrobacterium. Second, the resulting Agrobacterium strain is used to transform plant cells. Thus, for the generalized plant expression vector, the plasmid contains an origin of replication that allows it to replicate in Agrobacterium and a high copy number origin of replication functional in *E. coli*. This permits facile production and testing of transgenes in *E. coli* prior to transfer to Agrobacterium for subsequent introduction into plants. Resistance genes can be carried on the vector, one for selection in bacteria, for example, streptomycin, and another that will function in plants, for example, a gene encoding kanamycin resistance or herbicide resistance. Also present on the vector are restriction endonuclease sites for the addition of one or more transgenes and directional T-DNA border sequences which, when recognized by the transfer functions of Agrobacterium, delimit the DNA region that will be transferred to the plant.

In another example, plant cells may be transformed by shooting into the cell tungsten microprojectiles on which cloned DNA is precipitated. In the Biolistic Apparatus (Bio-Rad) used for the shooting, a gunpowder charge (22 caliber Power Piston Tool Charge) or an air-driven blast drives a plastic macroprojectile through a gun barrel. An aliquot of a suspension of tungsten particles on which DNA has been precipitated is placed on the front of the plastic macroprojectile. The latter is fired at an acrylic stopping plate that has a hole through it that is too small for the macroprojectile to pass through. As a result, the plastic macroprojectile smashes against the stopping plate, and the tungsten microprojectiles continue toward their target through the hole in the plate. For the instant invention the target can be any plant cell, tissue, seed, or embryo. The DNA introduced into the cell on the microprojectiles becomes integrated into either the nucleus or the chloroplast.

In general, transfer and expression of transgenes in plant cells are now routine practices to those skilled in the art, and have become major tools to carry out gene expression studies in plants and to produce improved plant varieties of agricultural or commercial interest.

Other Embodiments

All publications mentioned in this specification are herein incorporated by reference to the same extent as if each independent publication was specifically and individually indicated to be incorporated by reference.

While the invention has been described in connection with specific embodiments thereof, it will be understood that it is capable of flurther modifications. This application is intended to cover any variations, uses, or adaptations following, in general, the principles of the invention and including such departures from the present disclosure within known or customary practice within the art to which the invention pertains and may be applied to the essential features hereinbefore set forth, and follows in the scope of the appended claims.

We claim:

1. A method of producing a perennial grape embryogenic culture, said method comprising the steps of:
   (a) visually identifying an embryogenic cell or an embryogenic cell mass from a first grape explant culture, wherein said visually identified embryogenic cell or cells of said embryogenic cell mass are identified as having a white to pale yellow color;
   (b) transferring said visually identified embryogenic cell or embryogenic cell mass of step (a) to a second culture;
   (c) allowing said transferred embryogenic cell or embryogenic cell mass of step (b) to divide into additional embryogenic cells or embryogenic cell masses;
   (d) visually identifying an embryogenic cell or embryogenic cell mass of step (c), wherein said visually identified embryogenic cell or cells of said embryogenic cell mass of step (c) are identified as having a white to pale yellow color; and
   (e) transferring said visually identified embryogenic cell or embryogenic cell mass of step (d) to a third culture thereby producing a perennial grape embryogenic culture.

2. The method of claim 1, wherein said explant is obtained from anthers, ovaries, ovules, floral tissue, vegetative tissue, tendrils, leaves, roots, nucellar tissue, stems, seeds, protoplasts, pericycle, apical meristem tissue, embryogenic tissue, somatic embryos, or zygotic embryos.

3. The method of claim 1, wherein said explant is an explant of a variety selected from the group consisting of Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, Thomuscat, Aleatico, Alicante Bouschet, Aligote, Alvarelhao, Aramon, Baco blanc (22A), Burger, Cabernet franc, Cabernet Sauvignon, Calzin, Carignane, Charbono, Chardonnay CH 01, Chardonnay CH 02, Chardonnay CH Dijon, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, Zinfandel, Couderc 1202, Couderc 1613, Couderc 1616, Couderc 3309 (*Vitis riparia* X *rupestris*), Dog Ridge, Foex 33 EM, Freedom, Ganzin I (A×R #1), Harmony, Kober 5BB, LN33, Millardet & de Grasset 41B (*Vitis vinifera* X *berlandieri*), Millardet & de Grasset 420A, Millardet & de Grasset 101-14 (*Vitis riparia* X *rupestris*), Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris Constantia, Vitis california,* and *Vitis girdiana, Vitis rotundifolia, Vitis rotundifolia* Carlos, Teleki 5C (*Vitis berlandieri* X *riparia*), 5BB Teleki (selection Kober, *Vitis berlandieri* X *riparia*), SO$_4$ (*Vitis berlandieri* X *rupestris*), and 039–16 (*Vitis vinifera* X *Muscadinia*).

* * * * *

UNITED STATES PATENT AND TRADEMARK OFFICE
CERTIFICATE OF CORRECTION

PATENT NO.  : 6,455,312 B1
DATED       : September 24, 2002
INVENTOR(S) : Gray et al.

It is certified that error appears in the above-identified patent and that said Letters Patent is hereby corrected as shown below:

Column 2,
Line 17, "anunonium" should be -- ammonium --.

Column 6,
Line 4, "fingal" should be -- fungal --; and
Line 66, "Autumnu" should be -- Autumn --.

Column 7,
Line 3, "Niagrara" should be -- Niagara --.

Column 10,
Line 31, "embyogenic" should be -- embryogenic --; and
Line 33, "embryogensis" should be -- embryogenesis --.

Column 12,
Line 6, "particulary" should be -- particularly --.

Column 13,
Line 66, "fuision" should be -- fusion --.

Column 14,
Line 9, "development" should be -- development --.

Column 15,
Line 24, "of "Chardonnay" should be -- of "Chardonnay --.

UNITED STATES PATENT AND TRADEMARK OFFICE
CERTIFICATE OF CORRECTION

PATENT NO. : 6,455,312 B1
DATED : September 24, 2002
INVENTOR(S) : Gray et al.

It is certified that error appears in the above-identified patent and that said Letters Patent is hereby corrected as shown below:

Column 23,
Line 19, "flurther" should be -- further --.

Signed and Sealed this

Twenty-fourth Day of August, 2004

JON W. DUDAS
*Director of the United States Patent and Trademark Office*